(12) United States Patent
Freeman

(10) Patent No.: US 10,836,695 B2
(45) Date of Patent: Nov. 17, 2020

(54) PROCESS FOR RECOVERY OF GLYCEROL FROM BIODIESEL PRODUCTION STREAMS

(71) Applicant: A & C FREEMAN, Baston (GB)

(72) Inventor: Andrew Freeman, Baston (GB)

(73) Assignee: A & C FREEMAN, Baston (GB)

( * ) Notice: Subject to any disclaimer, the term of this patent is extended or adjusted under 35 U.S.C. 154(b) by 0 days.

(21) Appl. No.: 16/091,588

(22) PCT Filed: Apr. 7, 2017

(86) PCT No.: PCT/EP2017/058367
§ 371 (c)(1),
(2) Date: Oct. 5, 2018

(87) PCT Pub. No.: WO2017/174775
PCT Pub. Date: Oct. 12, 2017

(65) Prior Publication Data
US 2019/0161424 A1    May 30, 2019

(30) Foreign Application Priority Data

Apr. 7, 2016    (GB) .................................. 1605944.6

(51) Int. Cl.
*C07C 29/88*    (2006.01)
*C10L 1/182*    (2006.01)
(Continued)

(52) U.S. Cl.
CPC ............. *C07C 29/88* (2013.01); *B01J 19/245* (2013.01); *B01L 3/10* (2013.01); *C07C 29/76* (2013.01);
(Continued)

(58) Field of Classification Search
CPC ......... C07C 29/88; C07C 29/86; C07C 29/84; C10L 1/1826; C10L 1/02; C10L 2270/026; C10L 2200/0476; C10L 2290/543; C10L 2290/544; B01D 3/10; B01J 19/245; Y02E 50/13
See application file for complete search history.

(56) References Cited

U.S. PATENT DOCUMENTS

| 2009/0148920 A1 | 6/2009 | Schreck |
| 2009/0178928 A1* | 7/2009 | Groos ................ B01D 61/445 204/541 |

(Continued)

FOREIGN PATENT DOCUMENTS

| CN | 101481297 A | 7/2009 |
| CN | 104262102 A | 1/2015 |

(Continued)

OTHER PUBLICATIONS

Eaton et. al., Formulation and Combustion of Glycerol-Diesel Fuel Emulsions, 2014, ACS Publication, Energy and Fuels, vol. 28, pp. 3940-3947. (Year: 2014).*

(Continued)

*Primary Examiner* — Cephia D Toomer
(74) *Attorney, Agent, or Firm* — Nixon Peabody LLP; Ronald I. Eisenstein; Nicole D. Kling

(57) ABSTRACT

The present invention relates to a process for treating a glycerol solution comprising fatty acid soaps obtained in a biodiesel production process, to obtain a glycerol enriched phase.

10 Claims, 1 Drawing Sheet

(51) Int. Cl.
- *C07C 29/86* (2006.01)
- *C11C 3/00* (2006.01)
- *B01L 3/10* (2006.01)
- *B01J 19/24* (2006.01)
- *C07C 29/76* (2006.01)
- *C07C 29/84* (2006.01)
- *C10L 1/02* (2006.01)

(52) U.S. Cl.
CPC .............. *C07C 29/84* (2013.01); *C07C 29/86* (2013.01); *C10L 1/026* (2013.01); *C10L 1/1826* (2013.01); *C11C 3/003* (2013.01); *C10L 2200/0476* (2013.01); *C10L 2270/026* (2013.01); *C10L 2290/543* (2013.01); *C10L 2290/544* (2013.01); *Y02E 50/13* (2013.01)

(56) References Cited

U.S. PATENT DOCUMENTS

| | | | | |
|---|---|---|---|---|
| 2011/0004031 A1* | 1/2011 | Cruz | ....................... | C07C 29/88 568/870 |
| 2011/0056119 A1 | 3/2011 | Teo | | |
| 2011/0112336 A1* | 5/2011 | Macret | .................... | C07C 29/92 568/869 |
| 2012/0245371 A1* | 9/2012 | Lourenco | ................ | C07C 29/88 554/204 |
| 2012/0317875 A1 | 12/2012 | Awbrey et al. | | |
| 2014/0005424 A1* | 1/2014 | Jackam | ................... | C07C 67/03 554/167 |
| 2014/0256978 A1 | 9/2014 | Monguillon et al. | | |

FOREIGN PATENT DOCUMENTS

| | | |
|---|---|---|
| RO | 114603 B1 | 6/1999 |
| WO | 2015/006399 A1 | 1/2015 |

OTHER PUBLICATIONS

Emil et al., "Extraction and distillation process for producing purified glycerin." CAPLUS Database accession No. 2001-138618 abstract (Jun. 30, 1999).

Kocsisova et al., "G-phase from methyl ester production-splitting and refining." Petroleum and Coal 48(2):1-5 (2006).

* cited by examiner

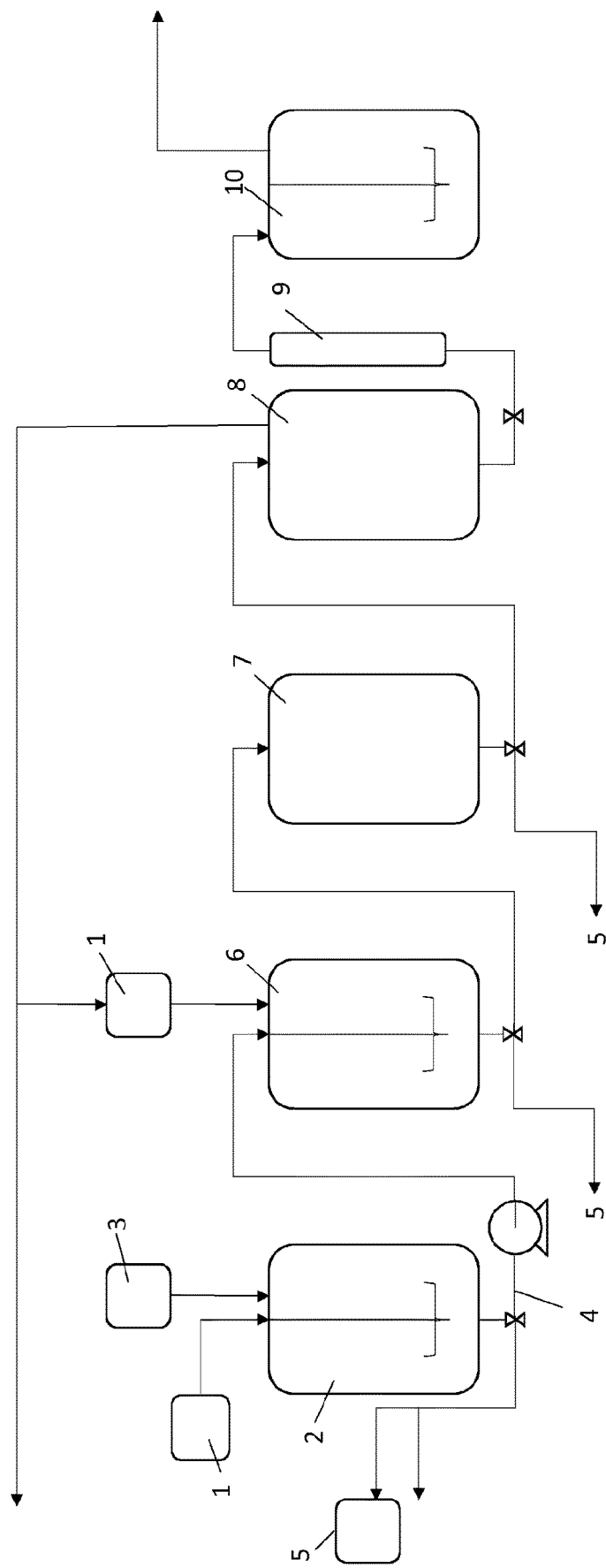

PROCESS FOR RECOVERY OF GLYCEROL FROM BIODIESEL PRODUCTION STREAMS

CROSS REFERENCE TO RELATED APPLICATIONS

This application is a 371 National Phase Entry of International Patent Application No. PCT/EP2017/058367 filed Apr. 7, 2017 which claims benefit under 35 U.S.C. § 119(b) of GB Application No. 1605944.6 filed Apr. 7, 2016, the contents of which are incorporated herein by reference in their entirety.

FIELD OF THE INVENTION

The present invention relates to a process for recovering glycerol, free fatty acids and other useful compounds from waste streams containing glycerol and fatty acid esters obtained in biodiesel transesterification reactions. It also relates to the use of a glycerol product thus obtained as a fuel component for compression ignition engines.

BACKGROUND OF THE INVENTION

Biodiesel and have become a legislatively required component of automotive diesel fuels in recent years. As a result, the level of biodiesel production has seen a significant increase in the last decennium, and is expected to increase with the amounts of biodiesel admixture to mineral oil based diesel required by the authorities.

Biodiesel contains alcohol esters of lipids, mainly mono alkyl esters such as methyl esters. The main constituent of natural oils and fats are acylglycerols, which term comprises triacylglycerols, diacylglycerols, and monoacylglycerols. The production of biodiesel entails the transesterification through alcoholysis with an aliphatic alcohol, typically methanol. The thus obtained fatty acid alcohol esters then form the main component of so-called "Biodiesel", as they can be combusted in internal combustion compression-ignition engines, often referred to as Diesel engines, and can be readily admixed with mineral oil derived fuel compositions.

These and similar esters of other lower aliphatic alcohols are typically produced in a transesterification process from animal fats and plant oils. The latter are largely composed of triglycerides, i.e. esters of three free fatty acids and glycerol, a trihydric alcohol (1,2,3-trihydroxypropane), alongside phospholipids and similar compounds.

In the alcoholysis, or transesterification process, a lower aliphatic alcohol, commonly methanol or ethanol, substitutes and thereby releases the glycerol backbone in a nucleophilic substitution reaction, typically under catalysis with strong bases such as sodium hydroxide, potassium hydroxide, and/or sodium methoxide. The transesterification reaction typically results in an apolar "fuel" phase comprising the transesterified ester components, and a highly polar aqueous glycerol phase or stream, also referred to as the "G-phase". This glycerol phase comprises the released glycerol, together with any components accumulated therein, including a proportion of unreacted fatty acids, and various mono- and di-esters, as well as phospholipids. Although quite limited, the mutual solubility characteristics of the organic and aqueous phases as well as the presence of highly effective emulsifiers in the form of the phospholipids results in significant yield loss of fatty acids and partially reacted glycerol products, while at the same time rendering the glycerol phase unsuitable as fuel or otherwise useful material. While attempts have been made to use these streams otherwise, e.g. as soil treatment as described in US-A-20140287917, or as an anti-icing compound, see for instance US-A-20120317875, these uses are rather limited.

Typically, biodiesel manufacturers combine additional waste streams comprising glycerol, as for instance obtained from washing, or distillation residue from the refining of the fuel product phases. Due to the presence of various compounds that cause issues in its use and in refining, these "G-phase" glycerol streams to date have found very little use. On the other hand, processes to refine these streams have so far met with difficulty.

Accordingly, there remains the need for a process that allows to remove the glycerol from the glycerol streams in an efficient and energy conserving manner. Furthermore, there remains the need to reduce the waste streams going to incineration, in particular since the streams also comprise water. Yet further, the remains the need to improve the overall yield and efficiency of the transesterification process by using the compounds in the waste streams.

SUMMARY OF THE INVENTION

Accordingly, in a first aspect the present invention relates to a process for treating a glycerol solution comprising fatty acid soaps obtained in a biodiesel production process, the process comprising the following steps: i. acidifying the glycerol solution with a concentrated acid under agitation to a pH in the range of from 0.5 to 2.5 and at a temperature of from 65 to 100° C. and allowing to phase separate into a first phase comprising free fatty acids; a second phase comprising a glycerol solution, and a third phase comprising salt and water; and ii. gravimetrically removing the free fatty acid phase and the salt phase from the glycerol solution, to obtain a glycerol enriched phase.

In a second aspect, the present process relates to an integrated process for the preparation of a biodiesel component and glycerol of high purity from a feedstock comprising vegetable oil and/or animal fats, comprising the steps of (i) alcoholysis of the vegetable oil and/or animal fats in the presence of a homogeneous base catalyst and a lower aliphatic alcohol, to obtain an ester phase comprising fatty acid aliphatic alcohol mono esters, and a glycerol solution comprising fatty acid soaps (G-phase) and salts, and (ii) separating the ester phase from glycerol solution comprising fatty acid soaps, and (iii) subjecting the glycerol solution to the separation process as set out herein above.

In yet a further aspect, the present invention relates to an apparatus equipped and configured for the preparation of a diluted dried glycerol composition according to the subject process, the apparatus comprising: a) at least one biodiesel transesterification reactor; and b) at least one neutralization and separator vessel; c) at least one drying unit fluidly connected to the neutralization and separator vessel; and d) a high vacuum distillation unit drying unit fluidly connected to the drying unit.

The disclosure also relates to a neutralized and dried glycerol composition, and to its use as fuel or fuel component for as suitably equipped combustion engine.

BRIEF DESCRIPTION OF THE FIGURE

FIG. 1 shows a schematic diagram depicting of an embodiment of the present process.

DETAILED DESCRIPTION OF THE INVENTION

As used herein, the term "base catalyst" refers to a base that catalyses a transesterification reaction of oil feedstock with at least one alcohol to produce biodiesel. Suitable base catalysts include but are not limited to alkali or earth sodium hydroxide and potassium hydroxide, or alcoholate, such as sodium methoxide.

As used herein, the term "neutralizing acid" refers to a concentrated mineral acid that causes dissociation of a fatty acid soap to produce free fatty acids. The acidification or neutralization reaction is one in which an acid and a fatty acid soap containing a base or alkali (soluble base) react and produce a free fatty acid and a salt, whereby the free fatty acid becomes soluble in a, organic solvent.

Suitable neutralizing acids include, but are not limited to, phosphoric, hydrochloric acid and sulfuric acid. The concentration of the acid preferably is at least 85%, more preferably at least 90%, and yet preferably at least 95% in order to limit the amount of water that is introduced into the system, and to limit the volume of the mixture that is to be separated. The acid is preferably a strong acid able to convert fatty acid salts into the free acids, thus an acid with a $pK_a$ of below 4.5.

A particular advantage of using a concentrated acid tis the fact that the neutralization reaction is strongly exothermic, which can deliver part of the energy required to dry and purify the glycerol.

As used herein, the term "fuel additives" refers to additives that are typically used in fuels, e.g. to avoid water ingression, or to increase certain properties, e.g. lubrication or viscosity.

As used herein, the term "fuel component" refers to components that ae typically added as combustible material to a fuel, to enhance or achieve certain properties, e.g. cetane numbers.

As used herein, the term "biodiesel" refers to a solution of alcohol esters of lipids produced in a transesterification reaction. For example, biodiesel can be produced by reacting feedstock with an alcohol, such as methanol to produce methyl esters. Suitable feedstock includes virtually any fats/oils of vegetable or animal origin. Examples of feedstock include but are not limited to butterfat, cocoa butter, milk fat, shea fat, borneo tallow, beef tallow, mutton tallow, tallow, lard, lanolin, rape seed oil, camelina oil, canola oil, castor oil, coconut oil, corn oil, cottonseed oil, hazelnut oil, hempseed oil, jatropha oil, mango kernel oil, meadow foam oil, mustard oil, linseed oil, olive oil, palm oil, palm kernel oil, peanut oil, rapeseed oil, rice bran oil, safflower oil, sasanqua oil, shea butter, soybean oil, sunflower seed oil, tall oil, tsubaki oil, tung oil, marine oils, menhaden oil, candlefish oil, cod-liver oil, orange oil, pile herd oil, sardine oil, whale oils, herring oils, triacylglycerols, diacylglycerols, monoacylglycerols, triolein palm olein, palm oil, palm stearin, palm kernel olein, palm kernel stearin, triglycerides of medium chain fatty acids, and derivatives, conjugated derivatives, genetically-modified derivatives and mixtures of any thereof.

As used herein, the term "transesterifying" refers to the reaction of a feedstock and a $C_1$-$C_6$ aliphatic monoalcohol in the presence of an alkaline catalyst. This reaction is typically followed by separating the glycerol-enriched soap stock, removing the catalyst residue and stripping off the lower alcohols. Transesterification may preferably be carried out with a suitable alcohol such as ethanol, isopropanol, n-butanol, i-butanol or t-butanol, most preferred of which being methanol.

This reaction is preferably carried out in the presence of a transesterification catalyst, such as metal alcoholates, metal hydrides, metal carbonates, metal acetates or various acids, in particular sodium alkoxide, sodium hydroxide and/or potassium hydroxide.

As used herein, the term "biodiesel process stream" refers to a solution containing biodiesel produced from a transesterification reaction. A biodiesel process stream may contain greater than or equal to 95% biodiesel.

The term "glycerol-enriched process stream," as used herein, is a composition comprising glycerol that is the product of the transesterification reaction set out above. The glycerol-enriched process stream also typically contains contaminants, including fatty acid soaps, and fatty acid mono- and diacetyl glycerol esters.

Preferably, the glycerol-enriched process stream comprises of from 20 to 80% by weight of glycerol, more preferably of from 40 to 75% by weight glycerol.

Typical compositions of the G-phase comprise about 65% w/w of glycerol, 10% w/w of free fatty acids, 10% w/w of partially unreacted mono-, di- and/or triglycerides; 5% w/w of so called soap stock, i.e. fatty acid alkali salts that are insoluble ion the G-phase, 5% w/w of methanol 5% and traces of water, mineral salts and fatty acid methyl esters. G-phase produced by using sodium hydroxide tends to be solid at room temperature, hence requiring heating to about 30° C. to liquefy, whereas G-phase produced by using potassium hydroxide tends to remain a liquid state at room temperature. In either case, the G-phase materials are perceived as brown to black in colour.

As used herein, the term "reduced glycerol-enriched process stream" refers to a glycerol-enriched process stream substantially free of fatty acids and fatty acids soaps, such as less than about 10% fatty acid soaps.

The term "salt," as used herein, refers to an alkali metal salt. Such salts include, but are not limited to NaCl, KCl, $Na_2SO_4$, $K_2SO_4$, $Na_2PO_3$, and $K_2PO_3$.

The term "fatty acid," as used herein, refers to a carboxylic acid with a long aliphatic tail (chain), which may be either saturated or unsaturated. In an embodiment, the fatty acid has between 8 and 24 carbons, in particular those derived from natural fats and oils as set out above.

As used herein, a "fatty acid soap" is a water soluble salt of a fatty acid. The fatty acid soap of the present disclosure can contain any cation that will render the fatty acid soap stock soluble in a polar solvent, such as water or glycerol. Such cations include but are not limited to such as sodium and potassium.

As used herein the term "homogenous catalyst" refers to a catalyst that is present in the same phase as the reactants, e.g., liquid reactants and liquid catalyst.

As used herein, "fluidly connected" means that a structure having at least two chambers has a passageway connecting the two chambers. The two chambers are fluidly connected if an intermediate chamber is fluidly connected to each of those two chambers. In other words, a system that is fluidly connected is capable of having fluid transfer from one part of the system to another.

The present disclosure provides significant advantages over prior glycerol and/or biodiesel manufacturing methods. Biodiesel is typically produced in a transesterification reaction between an animal or vegetable oil and an alcohol in the presence of a catalyst. Along with biodiesel, a glycerol solution containing salt and fatty acid soap is produced as a by-product.

The g-phase solution obtained in current biodiesel production processes is often either incinerated, or sent to a water treatment system after neutralization, requiring disposal, often even invoking high costs. While the glycerol solution may be used as microbiological feed component in anaerobic digesters, it needs careful adjustment of pH and salt concentration, while also causing excess foaming. Also the use in waste boilers is limited due to the relatively high water and salt content, which counters the need for relatively high temperatures to avoid the formation of acrolein during the process, which may require treatment of the flue gasses.

According to the present invention, crude glycerol process streams produced from biodiesel production are neutralized with little or no loss of glycerol using an two-step neutralization and de-esterification process, followed by removal of a fatty acid enriched stream, salts, water and methanol, and finally a vacuum distillation of the defatted, neutralised and dried and glycerol enriched stream. Thereby, the process according to the present invention advantageously results in no, or only a very low overall loss of glycerol obtainable from the biodiesel transesterification reaction, as well as delivering a highly concentrated glycerol product stream, if so desired. In this process, preferably, more than 85% of the glycerol is recovered, more preferably, more than 88% of the glycerol is recovered. The present disclosure therefore provides a biodiesel method that produces less waste as compared to prior methods.

EP2159212 discloses a method for purification of crude glycerol contaminated with alkaline salts. The disclosed method comprises the steps of: (a) combining the crude glycerol with at least 1 equivalent of sulfuric acid having a concentration of at least 85 wt %; (b) separating a glycerol layer from the salts; and (c) combining said glycerol layer with a solution of sodium borohydride and sodium hydroxide. In example 1 of D1, a stoichiometric amount of concentrated sulfuric acid is added to the solution, thereby neutralising the mixture, but not arriving at a pH of below 7, while the mixture arrives at 65° C. In example 2, a 0.25 molar excess of concentrated sulfuric acid is added to the solution, thereby not only neutralising the mixture, but also arriving at a low pH, which is however not disclosed, as is the temperature. The addition of borohydride to neutralise and react away the acid is however a relatively cumbersome exothermic reaction involving handling of solid borohydride, and generating hydrogen gas, and there is no neutralisation by a base.

In the subject process, a diluent is added to obtain a diluted glycerol enriched phase, and the neutralize the diluted glycerol enriched phase by addition of a base to obtain an aqueous phase comprising salts, and a glycerol enriched, neutralized and diluted phase. This gets gravimetrically separated again, into an aqueous phase and the glycerol enriched, neutralized and diluted phase.

CN103664523 discloses the dilution of the original crude glycerol phase with methanol, followed by neutralisation and filtration over a carbon bed.

US20140256978 discloses the use of sulfonic acids for the neutralisation, this an entirely different process. EP2308818 finally discloses the use of lower carboxylic acids, specifically acetic acids.

The present process has the advantage of allowing easy handling, and very fast reaction times with low water contents, and thus a smaller waste stream.

The transesterification reaction between the oil feedstock and an alcohol using a base catalyst may produce a biodiesel process stream and a glycerol rich process stream. Suitable base catalysts include, but are not limited to, sodium hydroxide, potassium hydroxide, sodium methoxide, potassium methoxide, or a combination of thereof. According to embodiments of the present disclosure, the biodiesel process stream may be separated from the glycerol rich process stream and removed for further processing, if necessary.

The glycerol process stream typically contain fatty acid soaps in addition to glycerol. The glycerol rich process stream is subsequently treated with an acid in a neutralization reaction that converts essentially all of the fatty acid soaps into insoluble free fatty acids. In a preferred embodiment, the salt that may be present in the glycerol process stream may be sodium chloride, potassium chloride, sodium sulphate, potassium sulphate or a combination of the salts.

Preferably, the concentrated acid solution is selected from hydrochloric, sulfuric and phosphoric acid comprising at least 70% by weight of acid, preferably at least 75%, more preferably at least 85% by weight of acid.

Preferably the subject process further comprises step (vi.) of removing the diluent and residual water from the diluted dried glycerol phase, to obtain a dried glycerol-enriched composition. The diluent preferably is a lower aliphatic alcohol, preferably wherein the aliphatic alcohol is selected from the group consisting of methanol, ethanol and n-isopropanol, most preferred being methanol. The diluent may after drying be recycled to any previous steps where it may be reused.

Preferably the subject process further comprises step (vii.) of subjecting the dried glycerol-enriched composition to a distillation under reduced pressure, to obtain a distilled glycerol composition.

Preferably, the base employed in step (iv.) comprises an alkali or earth alkali hydroxide, carbonate or alcoholate, preferably sodium hydroxide, preferably methoxide or ethoxide.

Preferably, the free fatty acid and/or methanol fractions are returned to a biodiesel production process as raw material streams.

By appropriately choosing the amount of water to be present in the process streams, an aqueous phase will separate off from the glycerol enriched phase, which allows decanting or otherwise physical removal of the glycerol enriched phase.

The glycerol-enriched stream or phase is then diluted, and subsequently subjected to drying. Advantageously, this done by neutralizing the thus far highly acidic phase, removal of a salt phase, and by distilling off from the neutralized phase, preferably under flash conditions, a proportion of the diluent along with the majority of the water still present in the glycerol-enriched, neutralized phase. Preferably, the diluent that is employed will form an azeotrope with the water, thereby effectively removing the water from the glycerol phase under relatively mild conditions.

The thus obtained dried glycerol phase is now largely comprised of glycerol, and a small portion of the diluent, but essentially void of water and salts. More preferably, the diluent is a lower alcohol that is also employed in the transesterification, i.e. ethanol, or in particular, methanol. The use of methanol throughout the process allows to simply streams and recycling of methanol to any of the stages where it is required, optionally after drying. Also, the use of a methoxides in the transesterification, and methanol in the system is also highly preferred, the first also useful for drying of methanol streams.

The defatted glycerol-enriched process stream may be subjected to distillation to remove the volatile components, such as methanol and/or water, to obtain a "crude glycerol" process stream comprising at least 95% glycerol. Crude glycerol is often purified by distilling the glycerol away from any remaining salts or polymeric compounds under reduced pressure, to yield a glycerol product comprising of at least 97%, preferably 98% of glycerol, or even to obtain a purified glycerol product, such as pharmacological grade glycerol comprising of more than 99% by weight of glycerol. However, it was found that this is difficult, and there is likely formation of acrolein in the glycerol if directly distilled off.

It is noted that some or all of the streams produced in the subject process may advantageously be returned to an appropriate position in the process or the biodiesel process. In this manner, an integrated process for the preparation of biodiesel and glycerol from a feedstock comprising vegetable oils or animal fat may be obtained, with high yields, and in high purity, and with a strongly reduced number and amounts of waste streams.

In a preferred embodiment of the present process, the transesterification reaction between the alcohol and oil feedstock may be carried out in a transesterification reaction vessel.

Efficient mixing of the alcohol, oil feedstock and catalyst in the reaction vessel can be accomplished in a variety of ways, including by the use of an impeller or other means of agitation.

Separation of the biodiesel from the glycerol-enriched solution and the salt phase may advantageously be achieved by allowing the reaction mixture to stand without agitation, or by use of a mixer settler unit.

The phases will separate out, and can then be removed from each other, for example, by draining the heavier salt phase, followed by the glycerol-enriched phase from the bottom of the reaction vessel, or by skimming the biodiesel phase from the top. In a preferred embodiment, the glycerol-enriched process stream may comprise of from 20 to 85% by weight glycerol, preferably of from 50 to 80% by weight of glycerol. This glycerol-enriched phase further comprises fatty acid soaps, and emulsifiers such phospholipids.

The glycerol-enriched phase is then suitably contacted with a neutralizing acid to release the water insoluble free fatty acids as a separate phase, resulting also in a fatty acid stream or phase, and a defatted, acidic glycerol process stream.

The term "acidifying" herein refers to the controlled addition of a concentrated acid in a suitable amount to a solution. This may be added to the glycerol stream, in an amount sufficient to not only to "neutralize" the basic streams exiting the transesterification reactor, but in a sufficient quantity to convert at least 80% by weight of the fatty acid salts to free fatty acids, preferably at least 90%, and more preferably at least 95% by weight of the fatty acid salts to free fatty acids.

Suitable neutralizing acid include hydrochloric acid, phosphoric acid and/or sulfuric acid, at a concentration of at least 90% by weight. This example is not intended to limit the disclosure as other suitable acids are known to one of skill in the art. The insoluble free fatty acids obtained in the neutralization reaction typically rise to the top of the glycerol-enriched process stream, and may then be separated off by one of a variety of methods known in the art, for example by decantation, or centrifugation, to yield a defatted glycerol-enriched process stream. A concentrated fatty acid phase, a concentrated defatted glycerol phase and an aqueous salt solution are the result of the acidification. Optionally, volatile components present in the glycerol-enriched process stream or glycerol-enriched defatted process stream may be removed alongside the fatty acids.

Such volatile components include, but are not limited to, methanol, ethanol, fatty acid methyl esters and fatty acid ethyl esters. The alcohol components, for example, may be unreacted alcohol from the transesterification reaction. Volatile components can be removed by a variety of methods. The glycerol-enriched process stream is finally placed in a vacuum reactor, whereby in order to reduce specific energy consumption the distillation unit preferably dos not employ a fractionation column, as this is not required in the present process. The vapours from the distillation can be condensed and stored for further use as e.g. fuel.

In further embodiments, the disclosure provides for an integrated process for producing biodiesel esters, fatty acids and glycerol, comprising combining an oil feedstock, an alcohol, and a homogeneous catalyst, thus producing an ester-enriched phase and a glycerol-enriched phase comprising fatty acid soaps; separating the ester-enriched phase from the glycerol-enriched phase; and contacting the glycerol-rich phase with an acid, thus converting the fatty acid soaps to free fatty acids.

As shown in FIG. 1, the present process permits to remove free fatty acids and salts may advantageously be removed from the glycerol rich process stream, leaving a defatted and desalted glycerol-enriched fraction or process stream.

In a preferred embodiment, the G-phase is fed from a preheater tank (1) at pH 11 to 14 is fed to the neutralisation reactor (2) equipped with a stirrer, an acid feed dosing vessel (3) linked to reactor (2) by a conduit. The reactor (2) further comprises a bottom conduit (4) comprising a looking glass and valve to drain separated off phases after phase separation. The salt phase may be moved to salt holding vessel (5); the fatty acid phase may be returned to a biodiesel process, or if integrated with, to a biodiesel reactor, and the glycerol enriched phase is preferably fed to a neutralisation reactor (6) equipped with a stirrer, bottom valve, methanol and alkaline feed conduit, and optionally, a settling tank (7). Reactor (6) or settling tank (7) is preferably linked to the drying vessel (8) linked to high vacuum distillation unit (9). In the neutralisation vessel (7), the enriched glycerol is neutralised to a pH in the range of from 6 to 8, and after removal of the lower salt phase, transferred to the drying vessel (8).

In this preferably air entrained drying distillation vessel (8), the enriched neutralised glycerol/methanol mixture is heated up under entraining air flow, and methanol and water vapours are removed from the head phase, from where in particular methanol can be returned to reactor 7 and/or to a biodiesel alcoholysis reactor. The thus dried glycerol material is preferably transferred to pre-heater (9) vacuum distillation unit (10) equipped with a vacuum installation, a heater and a distillation bridge that may be maintained at 160° C. Herein, the dried glycerol phase is subjected to a vacuum distillation, resulting in highly purified glycerol.

As set out above, the G-phase material is preferably fed to the reactor (2) from a preheating tank (1), wherein the material is heated to about 55 to 80° C. prior to processing. It is preferably constructed from an inert material such as stainless steel due to the corrosiveness of the materials, but may be made from other materials such as optionally coated mild steel. A suitable heating system may be employed for the preheating tank, which may employ any suitable design, but typically will be selected from one of the following systems: a.) an internal flat plate heat exchanger, with a heating fluid pumped around inside of the heat exchanger, preferably steam or water from a hot water tank or steam boiler; b.) external heating, e.g. whereby the tank can have a sealed outer skin with hot water pumped between the tank and the outer skin; c.) an external tube and shell heat exchanger for the G-phase feed to pass by the tubes of the heat exchange; d.) explosion risk proof immersion heaters with a suitably large surface area to produce a very low watt density. The selection of the heating equipment depends largely on the shape and volume, and surface to volume ratio, and can de designed accordingly by a skilled artisan. Generally, all of the equipment employed should be explosion risk proof, including any pumps to circulate the various material streams during the process.

The tank (1) may advantageously comprise a condenser to prevent any methanol or other volatile vapour loss to atmosphere. It preferably may also be fully insulated using commercially available chemical proof insulation to avoid heat loss.

Acid feed dosing vessel (3) is preferably also made from inert material, and preferably linked to reactor by a conduit comprising a metering pump to allow for controlled addition.

Neutralisation reactor (2) preferably is comprised of a material that can withstand the corrosive components employed, e.g. a suitable stainless steel grade. This material choice also applies to most of the other vessels and conduits.

Preferably the reactor is constructed with a coned or domed bottom and a large outlet in the middle of the bottom, preferably connected to a suitable conduit (4). A typical reactor is a continuously stirred tank reactor (CSTR) type.

Preferably, the reactor should have a heating system as outlined above, with the preferred method being internal heat exchangers. The stirring system preferably comprises a motor-driven stirrer with suitable baffles or the like, or may include a circulating pump drawing from the reactor bottom and returning to the top of the reactor.

The reactor may advantageously comprise a condenser to prevent any methanol or other volatile vapour loss to atmosphere. It preferably may also be fully insulated using commercially available chemical proof insulation to avoid heat loss.

Conduit (4) preferably comprises a valve and looking glass or other means of control, to allow for a separation of the phase separated materials during the decanting process, and is linked to at least neutralisation reactor (6)

Neutralisation reactor (6) preferably is a stainless steel construction with a coned or domed bottom and a large outlet in the middle of the bottom, to allow for the removal of the separated off salt phase after neutralisation. The tank preferably comprises a heating system that allows for heating of material, without forced motion of the material. Preferably methods a and b are used in this tank—either internal flat plate heat exchangers or a heated outer skin, both preferably heated by hot water or steam. The tank preferably is fully insulated similar to the pre-heating tank (1). Reactor (6) is suitably coupled to drying reactor (8) through an appropriate conduit. A settling tank (7) may be employed in between the reactors, in particular if the reactor (6) is designed as a smaller unit. From the reactor (6) or settling tank (7), a salt phase may be gravimetrically removed.

Drying reactor (8) may advantageously also be shaped in with coned or domed bottom and a large outlet in the middle of the bottom, similar to reactors 2 and 7. The tank may preferably be heated in a similar way to all tanks previous to allow for the material to reach a temperature of between 65° C. and 90° C. The reactor further may preferably be fully insulated, similar to previous tanks.

The preferably comprises a conduit in upper part of the reactor, for transferring methanol and water vapours, coupled to a suitable condenser and storage facilities, to capture the distilled off methanol and water vapour through a fractionation column or a vent in the reactor headspace.

The condenser preferably is designed and proportioned with sufficient cooling capacity to permit liquefaction of all methanol and water vapours, and linked to a receiving tank.

The drying reactor may employ an entrainment device, e.g. a spray bar fitted at top of the tank that is used to circulate the material to be dried, whereby material may be drawn from the bottom of the tank via a pump to the top of the tank, exiting through the spray bar in a fine mist. Compressed air or nitrogen may then be used in conjunction with the spray bar for aeration of the material, and to shift the hot vapour in the direction of the headspace and the condenser. Alternatively, a bubble flow reactor with entraining gas flow may be employed, whereby the compressed gas or air may be supplied to the bottom of the tank via suitable spargers driving air bubbles through the whole of the material. Either method may reduce the drying time required.

The distillation system may advantageously comprise of the following equipment: a pre-heating feed system; a heated vacuum distillation reactor, a condenser, a distillate receiving tank, a vacuum pump, and a heating system.

The feed preheating system may advantageously comprise a tube and shell heat exchanger, which may be fed from a reservoir tank containing glycerine enriched neutralized and dried material. Alternatively the feed preheating system may comprise a heated tank of stainless steel construction with e.g. internal flat plate heat exchangers fitted internally and/or a heated outer casing, the internal heat exchangers and heated outer casing typically being heated by thermal oil or steam.

The heat capacity of the feed preheater as well as of the reactor itself should be arranged as sufficiently high to heat the glycerine enriched material to a temperature of 160° C. upon entry to the heated vacuum reactor. It is understood that these two systems can be employed independently of each other, e.g. if a batch-wise operation is desired, or may be working in series to achieve the same temperature.

The heated distillation reactor preferably is constructed to support under reduced pressure of 10 mBar or below, at a temperature in excess of 200° C. It may advantageously have an outlet/inlet at the bottom, and/or well as several other out- or inlets at various levels into the reactor.

The reactor preferably should comprises an internal heat exchanger as well as the possibility to heat the entire outer casing in order to avoid any recycling of condensed glycerol vapours.

Preferably the reactor comprises a suitable stirring unit able to operate under high vacuum conditions, e.g. comprising a magnetic drive or a mechanically sealed stirrer shaft, or a circulating pump drawing glycerine rich material from the bottom of the reactor and returning it to the top of the reactor to induce liquid motion. Preferably the reactor tank may have series of temperature probes at various point in the reactor e.g. top, middle and bottom. Furthermore, the reactor preferably comprises a system to gauge the level of glycerine rich material, e.g. suitable sensors or floats. A condenser is linked to the head space of the reactor to capture the distilled-off glycerol vapours, either through a fractionation column or a vent in the reactor headspace. The condenser preferably is designed and proportioned with sufficient cooling capacity to permit liquefaction of glycerol and linked to a receiving vessel. The condenser preferably is maintained at a temperature of at least 40 to 80° C., preferably at least 60° C., to avoid low back of prematurely condensing glycerol, whereas the entire reactor is preferably maintained at least at the boiling temperature of the glycerol. Also the receiving vessel must support the vacuum in the system. A vacuum pump able to achieve a vacuum of between 1 to 10 mbar absolute pressures in the distillation system with suitable vapour traps is also part of the distillation system.

The invention also provides for an integrated process for the preparation of biodiesel component and glycerol from a feedstock comprising vegetable oil and/or animal fats, comprising the steps of i. alcoholysing the vegetable oil and/or animal fats in the presence of a homogeneous base catalyst and a lower aliphatic alcohol, to obtain an ester phase comprising fatty acid aliphatic alcohol mono esters, and a glycerol solution comprising fatty acid soaps and salts, and ii. gravimetrically separating the ester phase from glycerol solution comprising fatty acid soaps, and iii. subjecting the glycerol solution to the process as described herein above.

A schematic diagram of an example of an apparatus of the present invention is depicted in FIG. 1. While not shown, this scheme may be coupled to a biodiesel process, in a preferred embodiment, resulting in a fully integrated process. The biodiesel process combines a lower aliphatic alcohol, a homogeneous catalyst and oil feedstock. The alcohol optionally can be combined with the homogeneous catalyst before placing the solution into the bioreactor with the oil feedstock. Likewise, the oil feedstock can be combined with either the alcohol or the homogeneous catalyst before adding the solutions to the reactor. Oil feedstock, alcohol and base catalyst are introduced into the reaction vessel from an alcohol storage tank and oil storage through the use of pumps or the tanks are gravity feed tanks. The alcohol is typically introduced in a suitable ratio on the oil used. Optionally, prior to introduction of alcohol into the reaction vessel, catalyst may be blended with the alcohol. The catalyst is typically used in amount ranging from about 0.1% to about 2.0% by weight based on the oil used. Reaction times depend on the temperature of the reaction, catalyst type and amount, and amount of alcohol.

The glycerol-enriched phase from biodiesel synthesis is then neutralized with a concentrated strong acid, whereby the acid is chosen such as to be able to liberate the fatty acids. The sodium salts of fatty acids in the glycerol-enriched phase are thus converted to free acids, thereby becoming less soluble in the polar glycerol, and due to the low density, will float to the surface and are gravimetrically removed.

The present process also permits to prevent, or at least reduce polymerization and release of acrolein, as it allows operation at relatively mild temperatures, when distilling under a vacuum of below 100 mbar, preferably under 10 mbar, which reduces the boiling point of glycerol down to as low as 160° C.

In order to avoid flow back of condensing glycerol vapours, and hence an increase in the exposure to temperature and thus to formation of acrolein, Since glycerol vapours tend to the entire distilling equipment is preferably provided with heating elements to ensure that glycerol cannot prematurely condense, thereby reducing the throughput time and prolonged exposure to high temperatures.

The present invention also relates to a process for the preparation of a fuel composition comprising glycerol, and the use of the fuel composition in compressions ignition engines, such as those disclosed in U.S. Pat. No. 8,875,685.

Accordingly, it pertains also to a process comprising adding fuel additives and optional fuel components to the distilled glycerol composition, to obtain a glycerol fuel composition. The subject process preferably further comprises adding fuel additives and optional fuel components to the distilled glycerol composition, to obtain a glycerol fuel composition for a compression ignition engine. Optional fuel components include components that are suitable as combustion fuels.

The following non-limiting examples are provided to further describe the invention. Those of ordinary skill in the art will appreciate that several variations these examples are possible within the spirit of the invention.

Example 1

500 l of a viscous so called G-phase material produced by the transesterification of vegetable oils or animal fats using potassium hydroxide and methanol were introduced into a neutralization vessel equipped with a heating system, a mechanical stirrer, a dosing inflowing conduit, and a conduit at the bottom of the vessel that allowed to empty the vessel, and heated to a temperature of 65° C. The G-phase material had a pH of about 11, and a Specific gravity (Sg) of about 1.15 g/ml.

Once the G-phase had reached the above temperature, concentrated sulfuric acid (96% w/w) was gradually added to the G-phase under vigorous stirring in an amount of about 6% w/w on the G-phase used, i.e. until the G-phase mixture reached a pH of below 1.

During the addition, the temperature in the fluid in the reactor increased by about 15° C. in the mixture.

The thus neutralized mixture was then subjected to mixing for another 30 minutes at the temperature indicated above, and after mixing was stopped, allowing the mixture to settle for a further 30 minutes.

Already after a few minutes, the mixture had separated into three different layers or fractions, creating very clear definitions between products, and was ready for decanting. The phases were then separated by decantation, using a valve in the bottom of the reactor unit and a looking glass, resulting in three distinct fractions.

The bottom layer was a thick, creamy and slightly brownish material comprising about 5-10% of the total volume, and comprised mostly of 65-85% wt. of potassium sulphate and other salts, with a small proportion of glycerol, water and methanol.

The middle, glycerol-enriched layer comprised about 65-70% of the total volume, and was a slightly brownish translucent material with an oily consistency. Applicants found that it comprised mostly of glycerol, methanol and water, alongside traces of dissolved salts and various organic compounds.

The top layer comprising about 25-30% of the total volume was of a very dark reddish colour, and had an oily consistency. It comprised of about 90% wt. of free fatty acids, 5% wt. of methanol, 5% wt. of glycerol and a trace of salts, and could directly be reintroduced a process for the preparation of biodiesel.

The middle, glycerol enriched, layer was processed further to prepare for further purification, and had a pH of about 0.5 to 1.

This acidic glycerol enriched fraction was then introduced into a drying vessel equipped with a heater, stirrer and a compressed air entrainment system, and an overhead distillation unit, and maintained at 65° C. Then, about 20% v/v of methanol were added to this glycerol rich layer under thorough mixing, and then the layer was neutralized by addition of a solution of 20% of sodium hydroxide in methanol, until a pH of 7 was attained. After the neutralization was finished, the mixture was allowed to settle for a period of 2 hours, resulting in a phase separation for a lower layer comprising a salt fraction, and an upper layer comprising a glycerol enriched neutralized fraction.

The glycerol enriched neutralized top fraction comprised about 85-90% v/v of the entire mixture, and a brown, translucent material with an oily consistency, comprising mostly, but not solely of glycerol in an amount of about 80% wt., with as other components about 18% wt. methanol, the remainder comprising water, traces of salts and various organic compounds. The lower salt layer was then removed.

From the glycerol-enriched neutralized fraction, under a gas-entrained distillation, methanol and water were distilled off, leaving behind an essentially pure dried glycerol fraction having a pH of about 7.0, and containing only a very small proportion of methanol and water, whereby generally the amount of the latter was found to depend on the original G-phase feedstock.

The dried purified glycerol fraction was then subjected to a distillation under high vacuum, selecting the pressure to allow distillation of the glycerol at a temperature of below 170° C. in the reactor, to avoid dehydration to acrolein and formation of polymeric products. Care was taken to heat the entire still, including the upper parts to reduce recycling of prematurely condensing glycerol in order to limit the exposure to high temperatures.

The obtained distilled glycerol was a colourless liquid having a purity of higher than 99.1% wt. as determined by gas chromatography, at a high yield without any substantial loss of material, and as such found useful as fuel for glycerol burning compression engine without any additional additives. This was remarkable in that no fractionation column was employed throughout the entire process. Furthermore, the composition comprised no increased sulphur levels, although sulfuric acid had been employed initially.

Further purification, e.g. for the removal of water and any short chain fatty acids may applied including those using fractioned distillation, filtration and adsorption techniques, e.g. ion exchange resins or active carbon, or a membrane separation technology, the latter likely being the most effective to achieve very high purity glycerol, i.e. with a purity of above 99.5% wt., or higher, without loss of adsorption materials.

The invention claimed is:

1. A process for treating a glycerol solution comprising fatty acid soaps obtained in a biodiesel production process, the process comprising the following steps:
   i. acidifying the glycerol solution with a concentrated acid under agitation to a pH in the range of from 0.5 to 2.5 and at a temperature of from 65 to 100° C., and allowing the mixture to phase separate into a first phase comprising free fatty acids; a second phase comprising a glycerol solution, and a third phase comprising salt and water; and
   ii. gravimetrically removing the free fatty acid phase and the salt phase from the glycerol solution, to obtain a glycerol enriched phase, and
   iii. adding a diluent to obtain a diluted glycerol enriched phase;
   iv. neutralizing the diluted glycerol enriched phase by addition of a base to obtain an aqueous phase comprising salts, and a glycerol enriched, neutralized and diluted phase, and
   v. gravimetrically separating the aqueous phase and the glycerol enriched, neutralized and diluted phase.

2. The process according to claim 1, further comprising step (vi.) of removing the diluent and residual water from the glycerol enriched, neutralized, and diluted phase, to obtain a dried glycerol-enriched composition.

3. The process according to claim 2, comprising step (vii.) of subjecting the dried glycerol-enriched composition to a distillation under reduced pressure, to obtain a distilled glycerol composition.

4. The process according to claim 1, wherein the diluent is a lower aliphatic alcohol.

5. The process according to claim 4, wherein the lower aliphatic alcohol is selected from the group consisting of methanol, ethanol and n-isopropanol.

6. The process according to claim 1, wherein the concentrated acid solution is selected from hydrochloric, sulfuric and phosphoric acid comprising at least 70% by weight of acid.

7. The process according to claim 1, wherein the base employed in step (iv.) comprises an alkali or earth alkali hydroxide, carbonate or alcoholate.

8. The process according to claim 1, wherein the free fatty acid or methanol fractions, or both, are returned to a biodiesel production process as raw material streams.

9. The process according to claim 1, wherein the second phase comprising the glycerol solution process stream comprises of from 20 to 80% by weight of glycerol.

10. The process according to claim 3, further comprising adding fuel additives and optional fuel components to the distilled glycerol composition, to obtain a glycerol fuel composition for a compression ignition engine.

* * * * *